United States Patent
Klikovich et al.

(10) Patent No.: US 9,939,360 B2
(45) Date of Patent: Apr. 10, 2018

(54) WEAR INDICATOR IN A COMPOSITE SYSTEM OF REFRACTORY CERAMIC STONES

(71) Applicant: REFRACTORY INTELLECTUAL PROPERTY GMBH & CO. KG, Vienna (AT)

(72) Inventors: Michael Klikovich, Hinterbrühl (AT); Josse Bachmayer, Altmünster (AT); Karl Zettl, Vienna (AT); Alexander Maranitsch, Vienna (AT)

(73) Assignee: REFRACTORY INTELLECTUAL PROPERTY GMBH & CO. KG, Vienna (AT)

( * ) Notice: Subject to any disclaimer, the term of this patent is extended or adjusted under 35 U.S.C. 154(b) by 251 days.

(21) Appl. No.: 14/767,231

(22) PCT Filed: Mar. 13, 2014

(86) PCT No.: PCT/EP2014/054921
§ 371 (c)(1),
(2) Date: Aug. 21, 2015

(87) PCT Pub. No.: WO2014/170071
PCT Pub. Date: Oct. 23, 2014

(65) Prior Publication Data
US 2016/0084746 A1    Mar. 24, 2016

(30) Foreign Application Priority Data

Apr. 18, 2013   (EP) .................................. 13164347

(51) Int. Cl.
*G01N 3/56*    (2006.01)
*F27D 1/16*    (2006.01)
*F27D 21/00*   (2006.01)
*C21B 7/04*    (2006.01)

(52) U.S. Cl.
CPC ............. *G01N 3/56* (2013.01); *F27D 1/1621* (2013.01); *F27D 21/0021* (2013.01); *C21B 7/04* (2013.01)

(58) Field of Classification Search
CPC ..... G01N 3/56; F27D 1/1621; F27D 21/0021; C21B 7/04
USPC ........ 116/204, 208, 209; 73/431, 762, 866.5
See application file for complete search history.

(56) References Cited

U.S. PATENT DOCUMENTS

| | | | | |
|---|---|---|---|---|
| 4,385,752 A | * | 5/1983 | Hayashi | B22D 1/005 266/220 |
| 4,731,036 A | * | 3/1988 | Ulf | B63C 7/26 116/204 |
| 5,228,478 A | * | 7/1993 | Kleisle | B65G 53/523 116/208 |
| 5,421,561 A | | 6/1995 | Eisermann et al. | |

(Continued)

FOREIGN PATENT DOCUMENTS

RU    2243267 C1    12/2004

OTHER PUBLICATIONS

International Search Report for App. No. PCT/EP2014/054921 dated Apr. 23, 2014.

*Primary Examiner* — R. A. Smith
*Assistant Examiner* — Tania Courson
(74) *Attorney, Agent, or Firm* — Medley, Behrens & Lewis, LLC

(57) ABSTRACT

The invention relates to a wear indicator (display) in a compound system made of fireproof (refractory) ceramic bricks.

7 Claims, 4 Drawing Sheets

(56) References Cited

U.S. PATENT DOCUMENTS

Figure 1:
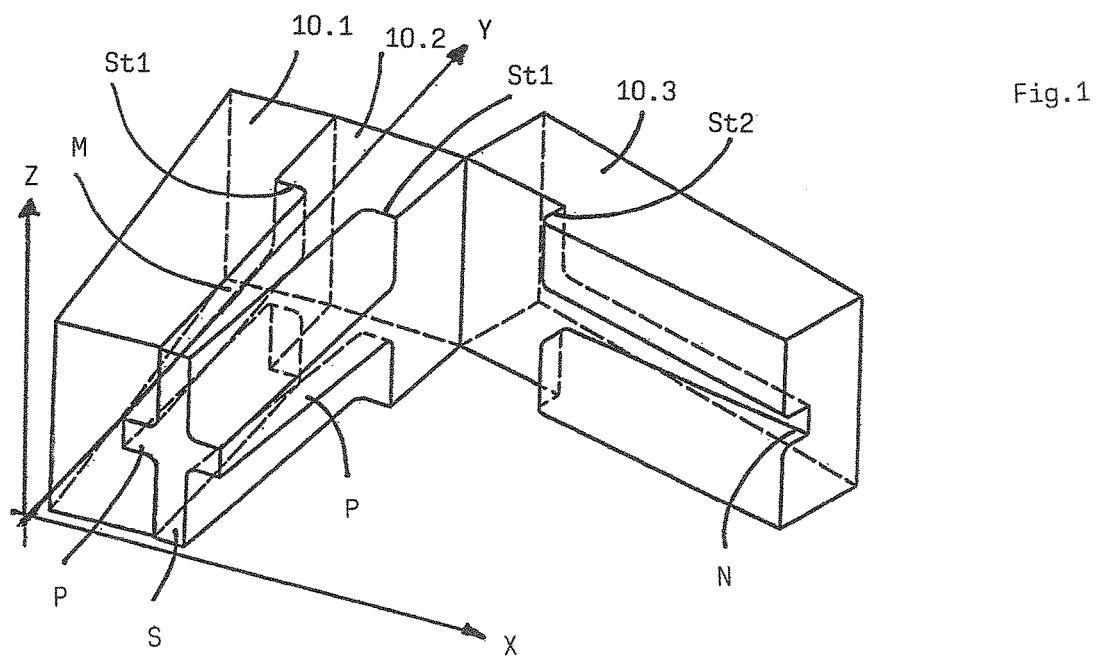

| | | | |
|---|---|---|---|
| 5,478,053 A | 12/1995 | Richter et al. | |
| 5,690,146 A * | 11/1997 | Stammen | F16L 11/124 |
| | | | 116/208 |
| 5,796,349 A * | 8/1998 | Klein | F16C 17/04 |
| | | | 116/208 |
| 5,947,053 A * | 9/1999 | Burnham | G01N 17/00 |
| | | | 116/208 |
| 6,390,908 B1 * | 5/2002 | Chen | B24B 37/32 |
| | | | 451/288 |
| 6,686,752 B1 | 2/2004 | Heumann et al. | |
| 2007/0175381 A1 * | 8/2007 | Harder | F16D 71/00 |
| | | | 116/208 |
| 2008/0295760 A1 * | 12/2008 | Wielstra | A46B 15/0002 |
| | | | 116/204 |

\* cited by examiner

WEAR INDICATOR IN A COMPOSITE SYSTEM OF REFRACTORY CERAMIC STONES

The invention relates to a wear indicator (display) in a compound system made of fireproof (refractory) ceramic bricks.

Fireproof ceramic bricks have been used for decades for the lining of industrial high temperature aggregates, for example furnaces. The state of the art and the invention are described further in the following by means of a metallurgic melting vessel. Such a metallurgic melting vessel, for example a tundish or a ladle, serves the reception, treatment and transfer of a metal melt. The vessel itself regularly features a metallic coating (envelope), which is, at least in the area of the base and the walls, protected by the mentioned lining made of fireproof ceramic bricks The fireproof ceramic bricks are subject to thermal, mechanical and metallurgic wear. For the safety of the vessel it is important that the protection of the coating is preserved to one hundred per cent in order to avoid the risk of an uncontrolled melt leak.

At the same time, the operator of the installation always tries to preserve the lining for as long as possible before it has to be repaired or replaced in order to keep the costs and downtimes as low as possible.

The decision when/if it is repaired and when/if it is replaced is to this date still made visually by the personnel which is in charge of the installation.

There have been attempts to measure the state of wear of the lining (the fireproof bricks) with the aid of measuring instruments. However, these measuring instruments, which then have to be arranged within the fireproof lining, are usually not sufficiently temperature resistant and also expensive.

Therefore the invention underlies the object to find a solution to indicate the wear within a compound system of ceramic bricks in a simple way.

To solve this problem, the invention originates from the following thought:

The wear indicator has to be arranged within the fireproof lining which is to be monitored. Due to the high temperatures which occur there, the wear indicator has to be made of a temperature resistant material. The easiest and most effective solution for this is to make the wear indicator of the same material of which the fireproof (refractory) lining is made.

An optimisation of these characteristics can be achieved when the wear indicator is part of the fireproof lining, and therefore also fulfils the function of the fireproof lining.

In order to fulfil the function of a wear indicator, the components of the wear indicator have to differ geometrically from the other bricks in the lining. This does not necessarily have to be valid for the entire geometry of the respective component. This aspect is much rather relevant insofar that the different geometries of the components of the wear installation have to be recognizable (visible) once the worn state is reached, at which an indication is to take place.

In other words: A conventional lining brick of a wall of a metallurgical vessel is usually defined as follows: The brick features a hot side, which is the side which is adjacent to the metal melt, and a cold side, which is the side which is adjacent to the outer metal coat of the vessel. The length of the brick (simplified in the following: Y-direction of the coordinate system) defines the distance between the hot side and the cold side. Due to wear, this distance is decreased in the y-direction, up to a critical degree of wear which is to be reported.

The idea of the invention is to make the geometry of the components of the wear installation clearly distinguishable from the geometry of the adjacent regular bricks of the lining, latest after reaching the critical degree of wear. This can then be visually recognized by the operating personnel, in fact very accurately, because the relevant change in geometry corresponds to a certain degree of wear.

In its most general embodiment, the invention relates to a wear indicator in a (for a) compound system (brickwork) made of fireproof ceramic bricks with the following characteristics:

the wear indicator consists of a set of at least two ceramic components (pieces)

each component features at least one surface segment with a three dimensional profile, wherein the profiles of corresponding surface segments of adjacent components complement one another in a form fitted manner, In the direction of wear of the components, the profiles either only extend over a partial length or with a different geometry or only over a partial length with a different geometry.

The direction of wear (Y) generally corresponds to a direction, which runs normal (perpendicular) to the inner surface of the refractory lining or rather to the corresponding furnace wall.

Especially at metallurgic vessels, which feature a generally cylindrical lining, it makes sense to design at least one component in such a way that it features a smaller cross sectional area at the segment which is subject to wear than at the segment which corresponds to the cold end of the component.

An alternative is the possibility to change the orientation of the component between the hot end and the cold end, for example to design the component (brick) at its hot end with a cross section which is generally orientated in the Z-direction (slim in the x-direction of the coordinate system and long in the Z-direction), while the cross section at the cold end features its largest extension in the X-direction. This can for example be achieved in such a way that the segment (part) of the component at the cold end protrudes on one or both sides in the X-direction compared to the segment of the component, which is adjacent to the hot end.

This change in the cross section, which corresponds to a change in the profile, must of course be noticeable enough so that the operating personnel can visually detect the change in geometry without troubles.

The mentioned profiles can be divided into two groups, namely male parts (protruding relative to adjacent surfaces) and female parts (recessed relative to adjacent surfaces).

In doing so the minimum, or rather maximum areas defined by the profiles should be at least 10%, better at least 20% or at least 30% different to the surface segments of the component arranged behind or in front in the Y-direction.

The profiles can be designed in different geometries, for example geometries from the group: bar, step, spike, bolt, pin, rib, pyramid, sawtooth, hole, channel, groove, prism, pitch circle, ellipse.

Each individual profile can be designed in such a way that in the direction of wear (Y) it enlarges in a direction (X, Z) perpendicular to the direction of wear (Y). For example at a bar-like profile, which extends in the Y-direction, a first segment in the direction of wear can have a cross sectional area a and a subsequent segment a cross sectional area which is Fa, wherein F can feature a value of 1.1, better 1.2 or 1.3, but preferably a value of at least 2 or 3 or 4.

The inverted profile, which, in the direction of wear (Y), diminishes in a direction (X, Z) perpendicular to the direction of wear (Y), is also possible.

At least one of the components can change its width (in the X-direction) in the direction of wear (Y). This particularly takes place perpendicularly to the direction of wear (Y). This can take place independently or simultaneously with the formation of the profile.

An embodiment where at least one component changes its height (in the Z-direction), perpendicular to the direction of wear (Y), in the direction of wear (Y), is also possible.

Each of these changes should again be at least 10%, better at least 20% or at least 30%, but preferable also at least double, triple, or quadruple of the original size.

The wear indicator may comprise two components, which interact, wherein generally only one component has to provide the desired wear indicator, while the other component only serves the purpose to create a form fitted connection to the other component so that the set of at least two components can be integrated in a form fit manner into the refractory lining.

A set of three or more components is also possible, wherein a middle (intermediate) component can be framed by two identically constructed, inversely arranged components.

The components can be particularly arranged vertically above each other or horizontally beside each other.

Besides the wear indicator, the invention also relates to an industrial aggregate, which is lined with fireproof ceramic bricks and features at least one wear indicator of the named type.

Multiple of such wear indicators can also be arranged within an aggregate, for example to indicate different wear conditions.

It is know that within a metallurgical vessel different sections of the lining are subject to different degrees of wear. It is therefore well possible to arrange a corresponding wear indicator, which functions independently from the other wear indicators, in each of these wear sections. Insofar the aggregate comprises multiple wear indicators of different designs. The different designs can be so that profiles and/or cross sections of the components of the wear indicator in the direction of wear (Y-direction) are arranged in different places.

Further characteristics of the invention arise from the characteristics of the sub claims as well as the further application documents.

The invention is further described in the following with the help of different embodiments. It is shown, each in a strongly schematic display, in FIG. 1: A three-part wear indicator in a perspective exploded view FIG. 2: a perspective exploded view of a second embodiment of a three-part wear indicator FIG. 3: the wear indicator according to FIG. 2 as part of a fireproof ceramic lining of a metallurgic vessel FIG. 4: a perspective exploded view of a two-part wear indicator In the figures, similar or similar acting elements (parts) of the wear indicator are labelled with the same reference characters.

FIG. 1 shows a wear indicator according to the invention made of three components 10.1, 10.2, 10.3. For further explanation a coordinate cross is additionally drawn.

The component 10.2 features the shape of a cross on its face S. A profile P with a rectangular cross section runs in the X-direction to the right and the left from the middle segment M which extends in the Z-direction.

In the Y-direction the middle segment M widens conically in the Y-direction. The bar-like profiles P remain unchanged in the X-direction, but conically widen upwards and downwards in the Z-direction, in fact up to a step St1, which parts the component 10.2 in the Y-direction approximately in a 2/3:1/3 ratio.

The segment which is longer in the Y-direction, which runs from the face S to the step St1, so at the hot side of the component 10.2, forms the segment of the component 10.2 which is allowed to wear, while the shorter segment, which is wider in the X-direction, defines the cold side of the component 10.2 and describes a minimum remaining thickness of the component 10.2 (in the Y-direction).

The components 10.1 and 10.3 arranged at the right and left in FIG. 1 are formed correspondingly to the component 10.2 with their side surfaces, which are allocated to the component 10.2, so that the components 10.1, 10.2 and 10.2, 10.3 can be assembled in a form fitted manner. This is displayed for the components 10.1 and 10.2, while the components 10.2 and 10.3 are displayed "folded apart", in order to make the corresponding profiles clearer. For example the component 10.3 features a groove N corresponding to the profile P of the component 10.2 as well as a step St2 analogue to the step St1.

Figure 2:
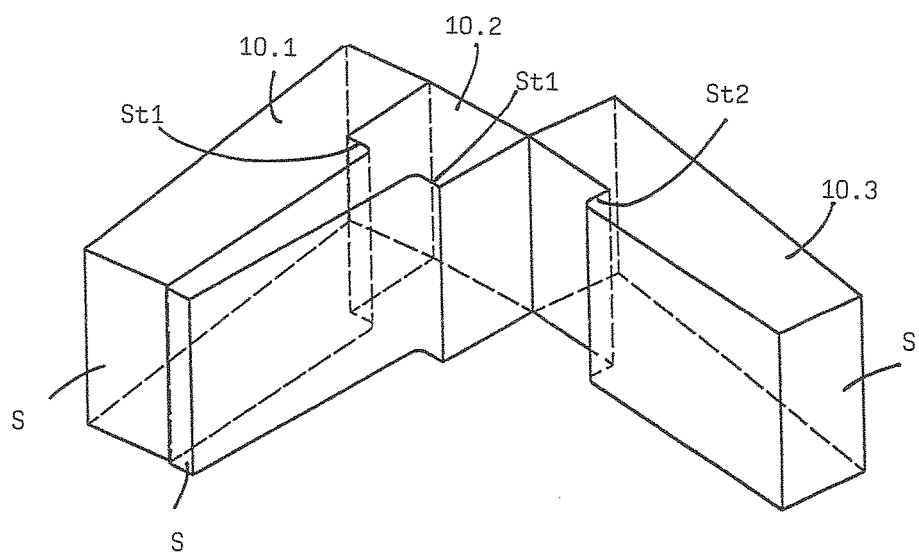

The embodiment according to FIG. 2 only differs to the embodiment according to FIG. 1 by the fact that that the bar-like profiles P at the component 10.2 and correspondingly the furrows N at the components 10.1 and 10.3 are missing. Apart from that the design and functioning of the wear indicator is identical.

Figure 3:
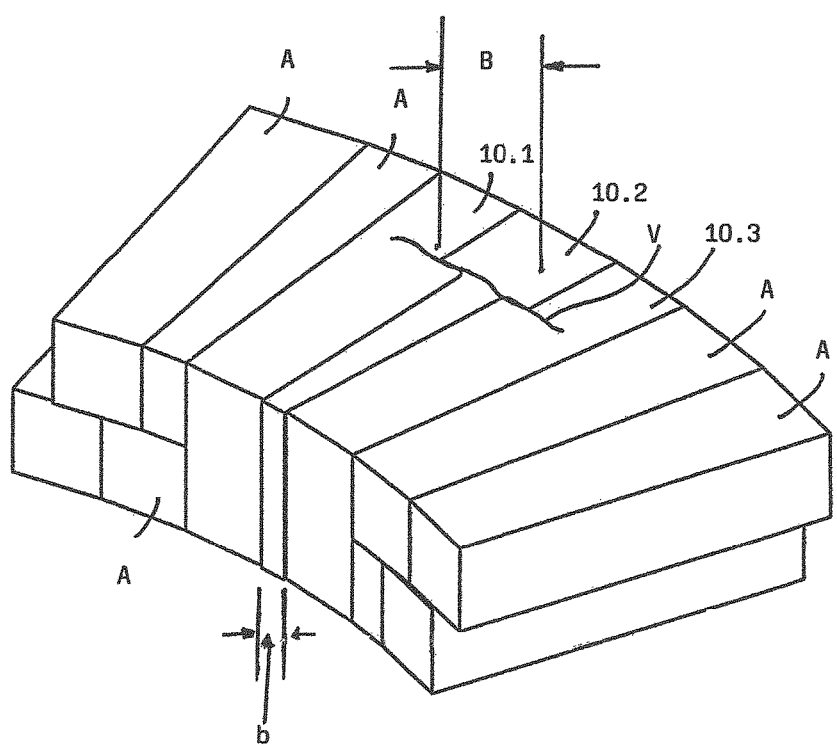

The set of components 10.1, 10.2 and 10.3 can form a part of a fireproof lining of a metallurgical vessel, which is displayed as a partial view of a tundish wall-lining in FIG. 3. Conventional lining bricks A can be seen at the left of component 10.1 as well as on the right of component 10.3. It can be seen, that the components 10.1, 10.2, 10.3 provide double the height (vertically, in the Z-direction of the coordinate system) of the adjacent bricks A of the lining. It is generally possible that the components (like 10.1, 10.2, 10.3) feature a height or width, which is a multiple, particularly an integer multiple, of the height or width of the normal lining bricks.

It is easy for the operating personnel to recognize when the lining is worn to the wear zone marked as a wavy line V, because the width (in the X-direction) b at the hot end of the component 10.2 is widening to a width B at the cold end of the component 10.2.

Figure 4:
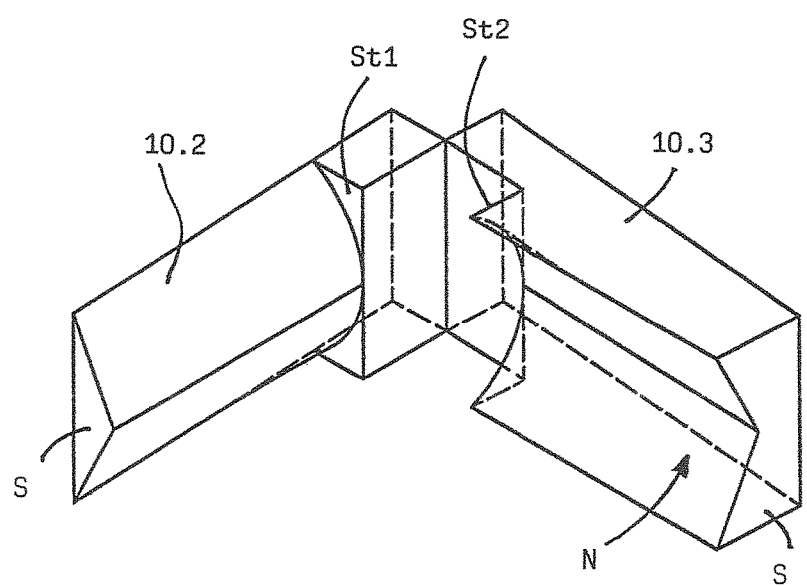

In the embodiment according to FIG. 4, the wear part of the component 10.2 is designed differently from the face S to the area of the step St1, in fact—in a vertical cross section—triangularly so that overall the geometry of a prism is created for the segment, onto which a segment with a rectangular cross section follows at the cold end of the component 10.2.

A pre-set wear limit can be detected optically when the wear brick 10.2 has changed its geometry from a triangle to a rectangle.

With this wear indicator one further brick is sufficient for the wear set, which is again labelled 10.3 and whose geometry is corresponding to the geometry of the component 10.2, in fact with a, compared to the furrow N according to FIG. 1, much larger furrow N, which is designed as a channel with a triangular cross section.

The invention claimed is:

1. Wear indicator in a compound system made of fireproof ceramic bricks (A) with the following characteristics:
   a.) the wear indicator consists of a set of at least two ceramic components (10.1, 10.2, 10. 3),
   b.) each component (10.1, 10.2, 10.3) features at least one surface segment with a three dimensional profile (P, N) from the group: bar, step, spike, bolt, pin, rib, pyramid, sawtooth, hole, channel, groove, prism, ellipse, pitch circle, wherein the profiles (P, N) of corresponding surface segments of adjacent components (10.1, 10.2, 10.3) complement one another in a form fitted manner, and with at least one profile (P, N) which, in a direction of wear (Y), downsizes in a direction (X, Z) perpendicular to the direction of wear (Y),
   c.) in the direction of wear (Y) of the components (10.1, 10.2, 10.3), the profiles (P, N) extend
      c1.) only over a partial length, or
      c2.) with a different geometry, or
      c3.) only over a partial length with a different geometry.

2. Wear indicator according to claim 1 with at least one profile (P, N) which, in the direct of wear (Y), enlarges in a direction (X, Z) perpendicular to the direction of wear (Y).

3. Wear indicator according to claim 1 wherein at least one component (10.1, 10.2, 10.3) changes its width (B), perpendicular to the direction of wear (Y), in the direction of wear (Y).

4. Wear indicator according to claim 1 wherein at least one component changes its height, perpendicular to the direction of wear (Y), in the direction of wear (Y).

5. Wear indicator according to claim 1 with a set of three components (10.1, 10.2, 10.3).

6. Industrial aggregate lined with fireproof ceramic bricks and comprising at least one wear indicator with the following characteristics:
   a) the wear indicator consists of a set of at least two ceramic components (10.1, 10.2, 10. 3),
   b) each component (10.1, 10.2, 10.3) features at least one surface segment with a three dimensional profile (P, N) from the group: bar, step, spike, bolt, pin, rib, pyramid, sawtooth, hole, channel, groove, prism, ellipse, pitch circle, wherein the profiles (P, N) of corresponding surface segments of adjacent components (10.1, 10.2, 10.3) complement one another in a form fitted manner, and with at least one profile (P, N) which, in a direction of wear (Y), downsizes in a direction (X, Z) perpendicular to the direction of wear (Y),
   c) in the direction of wear (Y) of the components (10.1, 10.2, 10.3), the profiles (P, N) extend
      c1.) only over a partial length, or
      c2.) with a different geometry, or
      c3.) only over a partial length with a different geometry.

7. Industrial aggregate according to claim 6 with multiple wear indicators of different shape.

* * * * *